United States Patent
Miller

(10) Patent No.: US 8,083,779 B2
(45) Date of Patent: Dec. 27, 2011

(54) ANCHOR ASSEMBLIES FOR SECURING CONNECTING ELEMENTS ALONG A SPINAL COLUMN

(75) Inventor: Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 489 days.

(21) Appl. No.: 12/261,686

(22) Filed: Oct. 30, 2008

(65) Prior Publication Data
US 2010/0114172 A1    May 6, 2010

(51) Int. Cl.
*A61B 17/70*    (2006.01)

(52) U.S. Cl. .................. 606/272; 606/264; 606/265

(58) Field of Classification Search .......... 606/250–278, 606/279, 246–249; 24/24, 20 R; 403/89, 403/92, 321, 322.1; 174/79
See application file for complete search history.

(56) References Cited

U.S. PATENT DOCUMENTS

| | | | | |
|---|---|---|---|---|
| 4,623,102 A * | 11/1986 | Hough, Jr. | .................. | 248/68.1 |
| 5,305,978 A * | 4/1994 | Current | ...................... | 248/230.4 |
| 5,367,750 A * | 11/1994 | Ward | .......................... | 24/16 PB |
| 5,593,125 A * | 1/1997 | Storz et al. | .................. | 248/316.5 |
| 5,622,341 A * | 4/1997 | Stana | .......................... | 248/74.1 |
| 5,662,653 A * | 9/1997 | Songer et al. | ................. | 606/270 |
| 6,004,349 A * | 12/1999 | Jackson | ........................ | 606/270 |
| 6,793,657 B2 * | 9/2004 | Lee et al. | ...................... | 606/269 |
| 2003/0004511 A1 | 1/2003 | Ferree | | |
| 2004/0182973 A1 * | 9/2004 | Kawai | ............................. | 248/71 |
| 2006/0142760 A1 * | 6/2006 | McDonnell | .................... | 606/61 |
| 2006/0229616 A1 | 10/2006 | Albert et al. | | |
| 2007/0161994 A1 | 7/2007 | Lowery et al. | | |
| 2009/0005813 A1 * | 1/2009 | Crall et al. | ..................... | 606/246 |
| 2010/0292739 A1 * | 11/2010 | Schwab | ........................ | 606/305 |

* cited by examiner

Primary Examiner — Thomas Barrett
Assistant Examiner — Jan Christopher Merene

(57) ABSTRACT

Devices and methods that securely engage an elongated connecting element in a receiver of an anchor assembly are provided. The anchor assembly includes an anchor member engageable to bony structure and the receiver includes a passage for receiving the connecting element when the connecting element is positioned along the bony structure. The anchor assembly includes an engaging member that engages the receiver and the connecting element to secure the connecting element in the receiver.

3 Claims, 3 Drawing Sheets

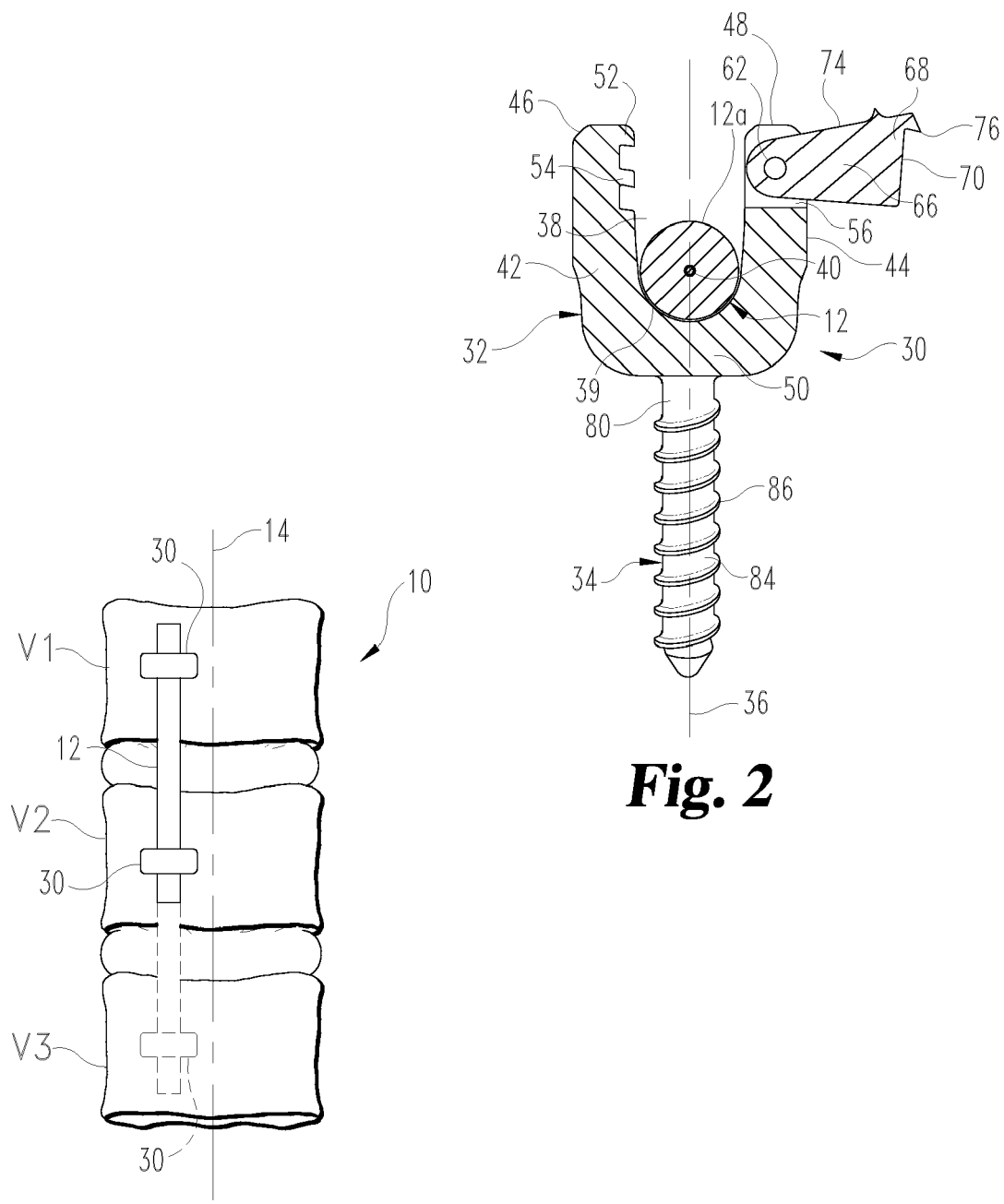

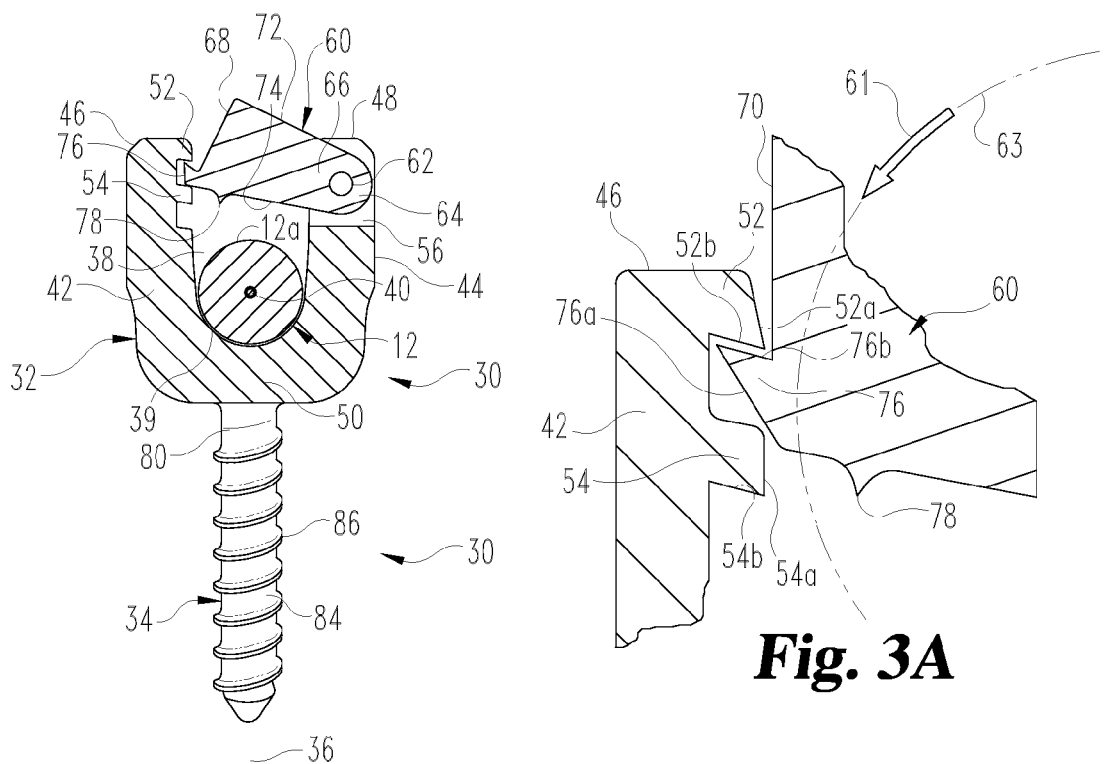
Fig. 3
Fig. 3A
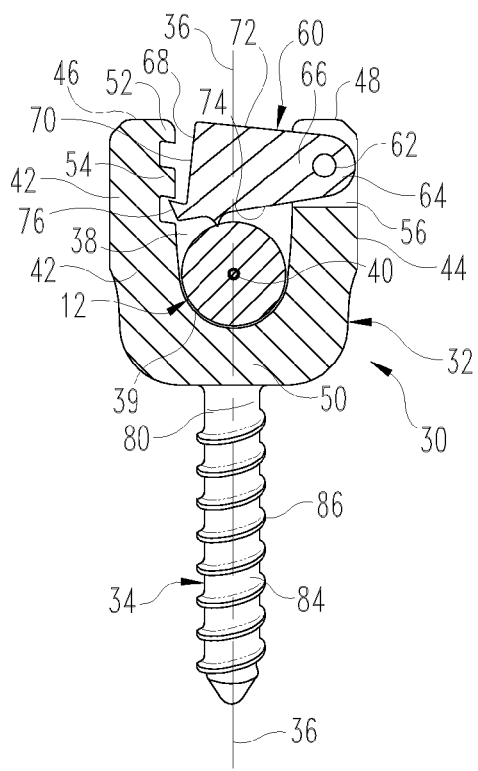
Fig. 4

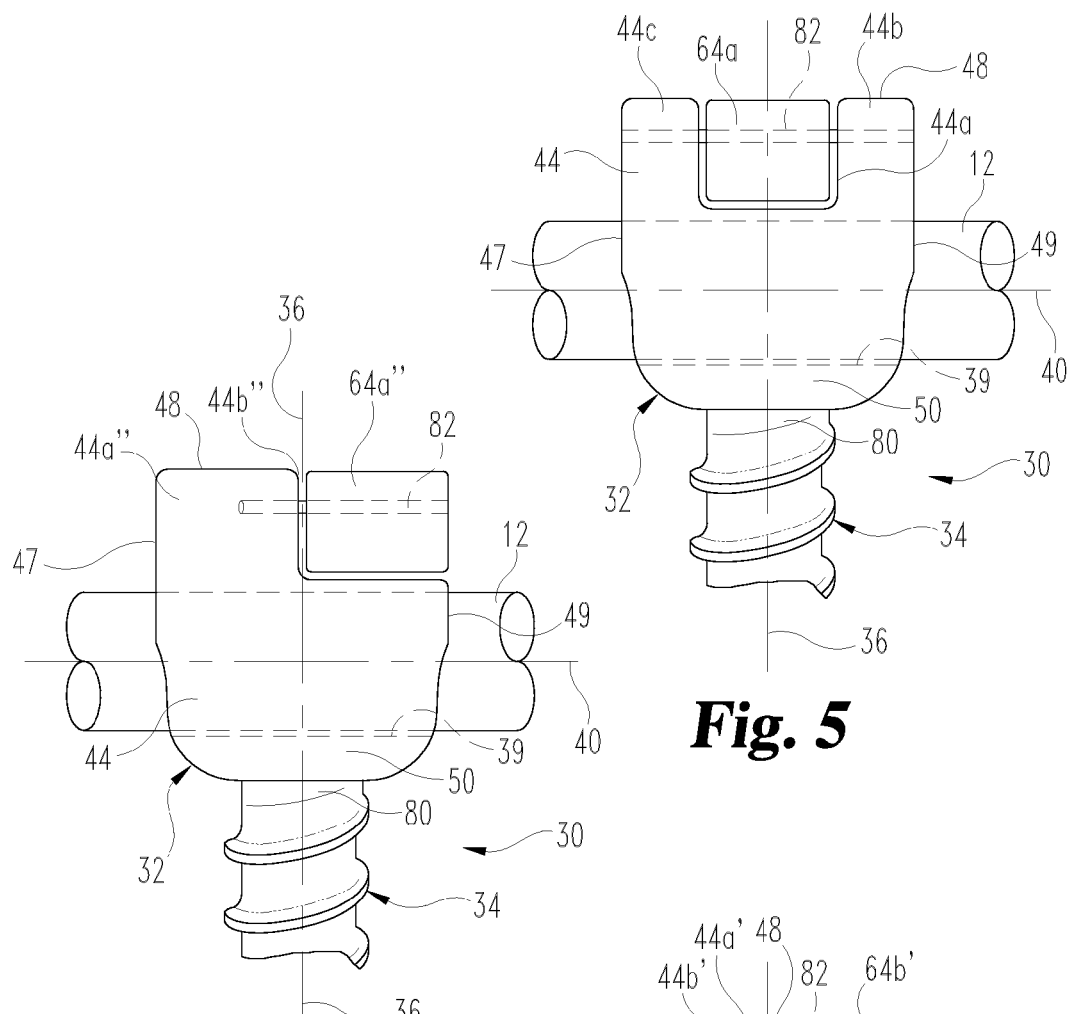
*Fig. 5*
*Fig. 7*
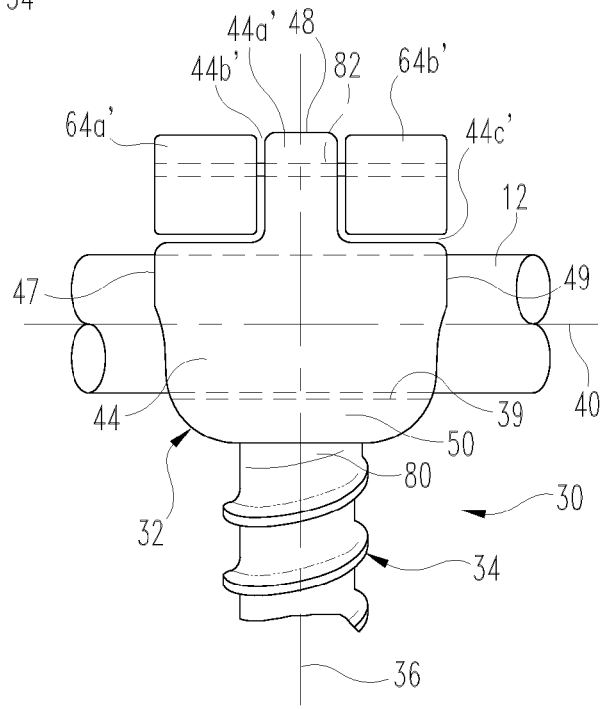
*Fig. 6*

ANCHOR ASSEMBLIES FOR SECURING CONNECTING ELEMENTS ALONG A SPINAL COLUMN

BACKGROUND

Elongated connecting elements, such as rods, plates, tethers, wires, cables, and other devices have been implanted along the spinal column and connected between two or more bone anchors engaged between one or more spinal motion segments. Such connecting elements can be positioned in the respective bone anchors with a top-down approach, a side-to-side approach, or a serial, endwise approach. In any event, it is desirable to securely engage the connecting element in the bone anchor to maintain the spinal stabilization effect provided by the connecting element when engaged between the bone anchors.

Typical implant and connection systems include several pieces, which commonly are useful and may be associated with only specific other pieces. Bone screws, hooks, and clamps are well known as spinal bone anchors, which are connected or adjoined to a particular bone as a connection between the bone and the connection system which can include an elongated connecting element that provides a support and/or stabilizing member. In such a system, a series of two or more bone anchors may be inserted into two or more vertebrae to be instrumented. A connecting element is then placed within or coupled to the bone anchors with engaging members, and the engaging members are tightened. In this way, a supporting structure is secured to the vertebrae, with the connecting element providing the support that promotes correction or healing of the vertebral malformation or injury. However, during surgery the connection of the connecting element to the bone anchors can be frustrating and time consuming for the surgeon due to intricacies involved in positioning the engaging member into the patient and securing it to the bone anchor. For example, the potential for cross-threading a set screw or nut to the bone anchor exists when threadingly coupling engaging members to the bone anchor. Also, the handling of small, intricate components for placement within the body during surgery and for interconnection with the bone anchor can also be time consuming and require great care on the part of the surgeon. Therefore, it would be desirable to minimize the number of components that are separately positioned within the body of the patient during surgery and to simplify the interaction between the various components.

SUMMARY

The present invention generally relates to devices and methods that secure an elongated connecting element in a receiver of an anchor assembly. The anchor assembly includes an anchor member engageable to bony structure and the receiver includes a passage for receiving the connecting element when the connecting element is positioned along the bony structure. The anchor assembly includes an engaging member that engages the receiver to secure the connecting element in the receiver.

According to one aspect, an anchor assembly for engaging a connecting element along the spinal column includes an anchor member engageable to a vertebral body, a receiver at a proximal end of the anchor member and an engaging member. The receiver includes a first arm and a second arm extending along a longitudinal axis proximally from the anchor portion to proximal ends of the first and second arms. The first and second arms define a passage therebetween that defines a second axis extending transversely to the longitudinal axis and the connecting element is positioned in the passage along the second axis. The first arm includes at least one projecting member extending into the passage proximally of the connecting element and the passage opens along the second axis at opposite sides of the first and second arms where the connecting element exits the passage and the passage opens at the proximal ends of the first and second arms. The engaging member includes a first end pivotally coupled to the second arm adjacent to the proximal end of the second arm. The engaging member extends from the first end to an opposite second, and the second end includes a locking member extending therefrom. The engaging member includes a first position when engaged to the receiver where the proximal end opening of the passage between the first and second arms is unobstructed to permit the connecting element to be positioned through the proximal end opening of the passage and the engaging member is pivotable about the pivot axis from the first position to a second position where the engaging member obstructs the proximal end opening and the locking member engages the projecting member to prevent the connecting element from passing through the proximal end opening of the passage.

According to another aspect, a bone anchor assembly includes an anchor member, a receiver at a proximal end of the anchor member defining a passage for receiving a connecting element therethrough and a connecting element extending along an axis through the passage. The receiver includes a first arm and a second arm extending along a longitudinal axis proximally from the anchor portion and transversely to the connecting element axis to proximal ends of the first and second arms. The passage opens along the connecting element axis at opposite sides of the first and second arms and the passage opens at the proximal ends of the first and second arms. The first arm includes first and second projecting members extending into the passage with the first projecting member being located adjacent to the proximal end of the first arm and the second projecting member being located distally of the first projecting member. An engaging member includes a first end pivotally coupled to the second arm adjacent to the proximal end of the second arm about a pivot axis, and the engaging member extends from the first end to an opposite second. The second end includes a locking member extending therefrom. The engaging member includes a first position when engaged to the receiver where the proximal end opening of the passage between the first and second arms is unobstructed and the engaging member is pivotable about the pivot axis from the first position to a second position where the engaging member obstructs the proximal end opening and the locking member engages at least one of the first and second projecting members to secure the engaging member between the first and second arms so that the engaging member obstructs the proximal end opening of the passage to prevent the connecting element from passing through the proximal end opening of the passage.

According to another aspect, a bone anchor assembly includes an elongated connecting element positionable along the spinal column, a bone anchor including a distal anchor portion and a receiver at a proximal end of the anchor portion, and an engaging member engaged to the receiver. The receiver includes a first arm and a second arm extending along a longitudinal axis proximally from the anchor portion to proximal ends of the first and second arms with the first and second arms defining a passage therebetween. The passage defines a second axis extending transversely to the longitudinal axis and the connecting element is positioned in the passage along the second axis. The passage opens along the second axis at opposite sides of the first and second arms where the connecting element exits the passage and the passage also opens at the proximal ends of the first and second arms. The first arm includes at least one projecting member extending into the passage proximally of a proximal-most side of the connecting element in the passage. The engaging member includes a first end pivotally coupled to the second arm about a pivot axis adjacent to the proximal end of the second arm with the pivot axis being located proximally of the proximal-most side of the connecting element. The engaging member extends from the first end to an opposite second, and the second end includes a locking member extending therefrom. The engaging member includes a first position when engaged to the receiver to permit the connecting element to be inserted in the passage from the opening at the proximal ends of the pair of arms and is pivotable about the pivot axis from the first position to a second position where the engaging member extends between the first and second arms and the locking member engages the projecting member to secure the connecting element in the passage.

These and other aspects will be discussed further below.

BRIEF DESCRIPTION OF THE DRAWINGS

FIG. 1 is a diagrammatic elevation view of a spinal column segment with a stabilization system attached thereto.

FIG. 2 is a partial section view of an anchor assembly and a connecting element in a receiver of the anchor assembly with an engaging member of the anchor assembly in a first position relative to the receiver.

FIG. 3 is a partial section view of the anchor assembly of FIG. 2 with the engaging member in a second position relative to the receiver.

FIG. 3A is an enlarged view of a portion of FIG. 3.

FIG. 4 is a partial section view of the anchor assembly of FIG. 2 with the engaging member in a third position relative to the receiver.

FIG. 5 is a partial elevation view of the anchor assembly showing one embodiment connection arrangement between the receiver and engaging member.

FIG. 6 is a partial elevation view of the anchor assembly showing another embodiment connection arrangement between the receiver and engaging member.

FIG. 7 is a partial elevation view of the anchor assembly showing one embodiment connection arrangement between the receiver and engaging member.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Devices and methods for securing a connecting element in an anchor assembly are provided for spinal and other bone stabilization surgical procedures. The anchor assembly includes a receiver for receiving the connecting element and a bone engaging portion to engage the anchor assembly and connecting element to bony structure. The anchor assembly includes an engaging member mounted to the receiver that is movable from a first position relative to the receiver that allows the connecting element to be positioned in the receiver to a second position where the engaging member contacts the receiver and secures the connecting element in the receiver. In one embodiment, the engaging member includes a third position relative to the receiver where the engaging member contacts the receiver and the connecting element to secure the connecting element in the receiver.

In FIG. 1 there is shown a spinal stabilization system 10 including at least one connecting element 12 releasably coupled to a plurality of anchor assemblies 30. Connecting element 12 includes one or more connecting elements or connecting element portions in axially extending relation to the spinal column. Connecting element 12 provides a construct between at least two vertebrae V1 and V2 to provide a desired stabilization effect to the spinal column. Connecting element 12 can be secured to at least one vertebra V1 with at least one first anchor assembly 30 and to at least one second vertebra V2 with at least one second anchor assembly 30'. Anchor assemblies 30 can be identical to one another, or include any one or combination of embodiments of anchor assembly 30 described herein. In another embodiment, only one anchor assembly 30 according to an embodiment discussed herein is used in system 10 while the other coupling devices are other anchors that secure connecting element 12 to one or more vertebrae.

The length of the construct between anchor assemblies 30 or anchor assembly 30 and other anchoring devices can be decreased or increased to extend along a single vertebral level as shown, or along two or more vertebral levels including vertebrae V1, V2, V3, and so on. System 10 can employ one connecting element 12 or multiple connecting elements 12 positioned along the same side of the central axis 14 of the spinal column, multiple connecting elements 12 positioned along opposite sides of central axis 14, or one or more connecting elements 12 positioned on central axis 14. The one or more connecting elements 12 can be engaged posteriorly along the spinal column to, for example, the pedicles of the vertebrae with one or more anchor assemblies 30. Other embodiments contemplate that connecting element 12 can be engaged laterally, antero-laterally, anteriorly or posteriorly to portions of the vertebra other than the pedicles.

In one embodiment, anchor assembly 30 includes a bone anchor with a bone engaging portion and a receiver with at least one passage for receiving the connecting element therein. The receiver includes at least one projecting member that extends into the passage, and the engaging member includes a body with a first end pivotally coupled to the receiver. The engaging member includes a second end opposite the first end with a locking member. The engaging member is mounted to the receiver while the bone engaging portion is engaged to the bony structure of the vertebra. The engaging member can be engaged to the receiver in a first position while the connecting element is initially maneuvered into the passage of the receiver, or engaged to the receiver after the connecting element is moved into the passage of the receiver. The engaging member is pivoted from its first position to a second position where the engaging member extends across the passage and the locking member engages the at least one projection to obstruct the opening of the receiver through which the connecting element was maneuvered, capturing the connecting element in the receiver. In one embodiment, the connecting element is movable relative to the receiver and the engaging member when the engaging member is engaged to the receiver in its second position, and the receiver includes a second projecting member so that the engaging member is movable from the second position relative to the receiver to a third position to engage the locking member to the second projecting member. In the third position, the engaging member contacts and fixes the connecting element in position relative to the receiver. In still another embodiment, the engaging member is positioned to function to either at least one of contact and fix the connecting element in position relative to the receiver when the engaging member is in the second position.

Referring to FIG. 2, there is shown a section view of a receiver 32 of one embodiment of anchor assembly 30 and one embodiment of bone engaging portion 34 extending distally from receiver 32 along a longitudinal axis 36. Connecting element 12 is positioned in passage 38 of receiver 32 and extends along a receiving axis 40. Receiving axis 40 extends transversely to longitudinal axis 36 so that connecting element 12 extends along the central axis 14 of the spinal column when bone engaging portion 34 is engaged to the underlying vertebra. Receiver 32 is joined to bone engaging portion 34 in a fixed relationship in the illustrated embodiment. Other embodiments contemplate the receiver 32 is multi-axial or pivotal relative to bone engaging portion 34 so that receiver 32 is rotatable and/or pivotal around bone engaging portion 34. Engaging member 60 is engaged to receiver 32 and pivotal relative thereto for movement between a first position shown in FIG. 2, a second position shown in FIG. 3, and a third position shown in FIG. 4.

Receiver 32 includes a pair of arms 42, 44 extending generally parallel to one another in the direction of longitudinal axis 36, and arms 42, 44 define passage 38 therebetween. Passage 38 opens at the proximal ends 46, 48 of arms 42, 44 to allow connecting element 12 to be top-loaded into passage 38 through the proximal end opening of passage 38 between arms 42, 44 for seating against or adjacent to bottom surface 39 of passage 38. Passage 38 also opens at the opposite sides of arms 42, 44 so that connecting element 12 extends from and exits passage 38 at the opposite sides 47, 49 of arms 42, 44 along receiving axis 40, as shown in FIGS. 5-7. Arms 42, 44 extend distally from proximal ends 46, 48 to a distal portion 50 that is mounted to a proximal end 80 of bone engaging portion 34. The external surfaces of arms 42, 44 can be curved around longitudinal axis 36, or can be non-curved and include surface features (not shown) that facilitate engagement of various instruments, such as driving instruments, reducers, and compression and distraction instruments, that can be employed in driving bone engaging portion 34 into bone and manipulating anchor assembly 30 after it is engaged to bone to re-position the bone, receiver 32, and/or anchor assembly 30.

Adjacent to proximal end 46 of arm 42, receiver 32 includes a first projecting member 52 that extends into passage 38. Arm 42 also includes a second projecting member 54 extending to passage 38 that is located distally of first projecting member 52. As discussed further below, the configuration of engaging member 60 allows an arrangement where only one of arms 42, 44 is provided with projecting members that secure engaging member 60 in position in receiver 32, allowing the size of receiver 32 to be minimized and further minimizing the intricacies of receiver 32 to engage engaging member 60. Furthermore, arms 42, 44 can be non-threaded and engaging member 60 is engaged to arms 42, 44 in a non-threaded arrangement. However, arrangements where the other or both of arms 42, 44 includes projecting members or other structures are not prohibited.

Second arm 44 includes a mounting portion 56 adjacent to proximal end 48. Engaging member 60 is pivotally mounted to second arm 44 at a mounting portion 56 of second arm 44 along a pivot axis 62. Pivot axis 62 is oriented parallel to receiving axis 40 to facilitate movement of engaging member 60 from its first position to its second and third positions, and so that the proximal end opening of passage 38 between arms 42, 44 can be provided in an unobstructed condition that permits insertion of connecting element 12 even when engaging member 60 is mounted to receiver 32 in its first position of FIG. 2. Engaging member 60 includes a first end 64 that is pivotally mounted to mounting portion 56 about pivot axis 62. Engaging member 60 includes a body 66 that extends from first end 64 to an opposite second end 68. Second end 68 includes a side surface 70 that extends between an upper end 72 and a bottom end 74 of engaging member 60. A locking member 76 projects outwardly from side surface 70 in a direction away from first end 64.

Engaging member 60 includes a first position shown in FIG. 2 where it is pivoted about pivot axis 62 so that the proximal end opening between arms 42, 44 is unobstructed to permit placement of connecting element 12 into passage 38 while passage 38 remains substantially intact to provide a receptacle to receive connecting element 12. From this first position, engaging member 60 is pivotal about pivot axis 62 to its second position in FIG. 3 where locking member 76 is engaged between projecting members 52, 54. In this second position, connecting element 12 is captured in passage 38 and cannot move back through the proximal end opening of arms 42, 44 to escape passage 38. In the illustrated embodiment of FIG. 3, engaging member 60 does not contact connecting element 12 when engaging member 60 is in the second position, allowing adjustments in the relative positioning between connecting element 12 and anchor assembly 30 to be performed by the surgeon.

From the second position of FIG. 3, engaging member 60 is rotatable about pivot axis 62 to its third position shown in FIG. 4. In the third position, locking member 76 is engaged to the distal side of second projecting member 54 and engaging member 60 contacts connecting element 12 to secure connecting element 12 in position relative to anchor assembly 30. In the illustrated embodiment, engaging member 60 includes at least one extension 78 that contacts connecting element 12. Extension 78 extends from bottom end 74 to positively engage connecting element 12. Extension 78 can be in the form of a spike or protrusion that at least partially enters, penetrates, deforms or contacts connecting element 12 to fix it in position in receiver 32. Other embodiments contemplate that multiple extensions 78 are provided to enter connecting element 12. In still other embodiments, the one or more extensions 78 do not enter connecting element 12, but provide surface features that enhance the frictional contact of engaging member 60 against connecting element 12 to fix connecting element 12 in position in receiver 32. In still other embodiments, extension 78 is not provided and bottom end 74 of engaging member 60 contacts connecting element 12 to fix it in position in receiver 32.

Locking member 76 of engaging member 60 engages a respective one of the projecting members 52, 54 in a one-way ratcheting type arrangement in the illustrated embodiment, shown in further detail in FIG. 3A. Locking member 76 includes a distal face 76a that slides along the outer ends 52a, 54a of the respective projecting members 52, 54 as locking member 76 is moved along the respective projecting member 52, 54. Locking member 76 and/or the respective projecting member 52, 54 can flex to accommodate movement of distal face 76a past the outer end 52a, 54a when locking member 76 is pivoted about pivot axis 62 along arced path 63 and distally into passage 38 in the direction of arrow 61. When distal face 76a advances distally beyond the respective outer end 52a, 54a, locking member 76 extends into the space distally of the respective projecting member 52, 54 so that proximal face 76*b* of locking member 76 contacts distal face 52*b*, 54*b* of the respective projecting member 52, 54 to prevent locking member 76 and engaging member 60 from rotating in the direction opposite arrow 61. Accordingly, distal face 76*a* is oriented more tangentially to the rotational arced path 63 of locking member 76 about pivot axis 62, while proximal face 76*b* and distal faces 52*b*, 54*b* are oriented more orthogonally to the rotational arced path 63 of locking member 76 about pivot axis 62.

When engaging member 60 is in the third position of FIG. 4, upper end 72 is aligned with or recessed distally of proximal ends 46, 48 of arms 42, 44 to limit or avoid any structure that projects into adjacent tissue proximally from arms 42, 44. Bottom end 74 is shown in an oblique orientation to upper end 72 to minimize the size of first end 64 where it connects with arm 44 and provide sufficient space in passage 38 distally of engaging member 60 to accommodate connecting element 12. In the illustrated embodiment, pivot axis 62 is located proximally of the proximal-most side 12*a* of connecting element 12 when positioned in passage 38. This provides arms 42, 44 with sufficient height along longitudinal axis 36 to form a passage 38 that extends from bottom surface 39 to at least proximal side 12*a* of connecting element 12 so that connecting element 12 is confined in passage 38 between arms 42, 44 even when engaging member 60 is in its first position.

In a further embodiment, it is contemplated that arm 42 only includes one projecting member 52 or 54. The single projecting member in passage 38 can be located to permit engaging member 60 to be secured in the second position of FIG. 3 in one arrangement, allowing connecting element 12 to move relative to receiver 32 when engaging member 60 is pivoted from its first position to engage the single projecting member of receiver 32. In another arrangement, the single projecting member is located so that engaging member 60 contacts and fixes connecting element 12 in receiver 32 as shown in FIG. 4 when engaging member 60 is rotated from its first position to engage the single projecting member of receiver 32. In still other embodiments, more than two projecting members are provided along arm 42 that extend into passage 38 to allow variability in the placement of engaging member 60 relative to connecting element 12 and the degree to which engaging member 60 fixes connecting element 12 in passage 38. In still another embodiment, engaging member 60 includes two locking members 76 extending therefrom, and arm 42 includes a single projecting member in passage 38. Other embodiments contemplate other arrangements where arm 42 includes one or more projecting members and engaging member 60 includes one or more locking members 76. The number of engaging members and locking members can be the same on a particular embodiment, or can differ from one another in a particular embodiment.

As shown in FIGS. 5-7, various connection arrangements between arm 44 and engaging member 60 are contemplated. In FIG. 5, arm 44 defines a receptacle 44*a* that opens at proximal end 48 and into passage 38 and the side of arm 44 opposite passage 38. First end 64 of engaging member 60 includes an ear 64*a* that is positioned in receptacle 44*a*, and is pivotally coupled to opposite hubs 44*b*, 44*c* defined by arm 44 on opposite sides of receptacle 44*a*. A pin 82 can be provided that extends through engaging member 60 and into bores in hubs 44*b*, 44*c* to provide the axis about which engaging member 60 pivots. Pin 82 can be a completely separate component from arm 44 and engaging member 60 in one embodiment. In another embodiment, pin 82 is formed as a unitary structure with engaging member 60 or with one or both of hubs 44*b*, 44*c*.

In FIG. 6, arm 44 includes a single, central hub 44*a*' at its proximal end 48 rather than a central receptacle. Opposite side receptacles 44*b*', 44*c*' are provided on opposite sides of central hub 44*a*'. Engaging member 60 include opposite ears 64*a*', 64*b*' at first end 64 that are received in receptacles 44*b*', 44*c*' and coupled to central hub 44*a*' with one or more pins 82.

In FIG. 7, arm 44 includes a single hub 44*a*" at its proximal end 48 and a single receptacle 44*b*". Engaging member 60 includes an ear 64*a*" at first end 64 that is received in receptacle 44*b*" and coupled to hub 44*a*" with one or more pins 82. In these embodiments, pin or pins 82 may be unitary structures with the respective hub or hubs of arm 44 or the ear or ears of engaging member 60.

As shown in FIG. 2, anchor member 34 can be a bone screw having an elongated shaft 84 extending distally from receiver 32 along a longitudinal axis 36. Shaft 84 can include an external thread profile 86, and can be solid or include a lumen extending axially therealong. The proximal end of shaft 84 can open into a tool recess in receiver portion 32 or at the proximal end 80 of shaft 84 to receive a driving tool to facilitate driving anchor member 34 into a bony structure, such as a vertebral body. Receiver 32 can be fixed relative to bone anchor 34 or bone anchor 34 can be pivotally captured in receiver 32 to allow shaft 84 to pivot relative to receiver 32. The uni-axial anchor assemblies provide a fixed positioning of the receiver relative to the anchor member. The pivotal arrangement allows the multi-axial anchor member to be positioned relative to the receiver and connecting element at various angles relative to one another. Such variable positioning can facilitate placement of the connecting element into receiver 32 even when the anatomical conditions prohibit or make difficult a linear arrangement of the connecting element between anchor assemblies.

Other embodiments contemplate other forms for the anchoring member. In other embodiments, the distal anchor member can be in the form of a hook, staple, cable, tether, suture anchor, interbody fusion implant, artificial disc implant, bolt, or other structure engageable to bony tissue. The receiver defines a passage that receives a connecting element, such as a rod, tether, wire, cable, plate or other elongated linking member that can extend between one or more additional anchor assemblies secured to one or more additional vertebrae or other bony structure.

The anchor members can be configured as pedicle screws, bolts or other member sized and configured for engaging a pedicle of vertebra. The anchor member can also be configured to engage other parts of a vertebra, or other bony structures in the patient. Furthermore, a set screw, washer, crown, cap or other device may be provided in addition to engaging member 60 for engagement within and/or about receiver 32 to secure connecting element 12 thereto.

Connecting element 12 can be a spinal rod connectable to one or more anchor assemblies to rigidly stabilize the spinal column. Connecting element 12 can also be flexible or include flexible portions to allow motion of the spinal motion segment or segments to which it is attached. It is also contemplated that connecting element 12 can be a single, unitary member or be comprised of multiple components. Various forms for the connecting element 12 are contemplated, including plates, wires, struts, cables, and other devices capable of engagement in a receiver of an anchor assembly with engaging member 60. Connecting element 12 can be a spinal rod comprised of any one or combination of metal, metal allow, plastic, polymer, tissue, fabric, or mesh material, for example.

While the invention has been illustrated and described in detail in the drawings and foregoing description, the same is to be considered as illustrative and not restrictive in character. All changes and modifications that come within the spirit of the invention are desired to be protected.

What is claimed is:

1. A bone anchor assembly, comprising:
an elongated connecting element positionable along the spinal column;
a bone anchor including a distal anchor portion and a receiver at a proximal end of said anchor portion, said receiver including a first arm and a second arm extending along a longitudinal axis proximally from said anchor portion to proximal ends of said first and second arms, said first and second arms defining a passage therebetween, said passage defining a second axis extending transversely to said longitudinal axis and said connecting element is positioned in said passage along said second axis, wherein said passage opens along said second axis at opposite sides of said first and second arms where said connecting element exits said passage and said passage opens at said proximal ends of said first and second arms, wherein said first arm includes at least one projecting member extending into said passage proximally of a proximal-most side of said connecting element in said passage; and
an engaging member including a first end pivotally coupled to said second arm about a pivot axis adjacent to said proximal end of said second arm with said pivot axis being located proximally of said proximal-most side of said connecting element, said engaging member extending from said first end to an opposite second end, said second end including at least one locking member extending therefrom, wherein said engaging member includes a first position when engaged to said receiver to permit said connecting element to be inserted in said passage through said proximal end opening of said passage and said engaging member is pivotable about said pivot axis from said first position to a second position where said engaging member extends between said first and second arms and said locking member engages said projecting member to prevent said connecting element from passing through said proximal end opening of said passage, wherein said engaging member includes a top end opposite a bottom end, which is oriented toward said proximal most side of said connecting member when said engaging member is in the second position, said top end being positioned in alignment with said proximal ends of said first and second arms when said engaging member is in said second position.

2. The bone anchor assembly of claim 1, wherein said engaging member includes an extension extending from said bottom end to fix said connecting element in position in said passage when said engaging member is in said second position.

3. The bone anchor assembly of claim 1, wherein said bottom end is spaced from said connecting element when said engaging member is in said second position.

* * * * *